United States Patent [19]

Saguchi et al.

[11] Patent Number: 5,503,839
[45] Date of Patent: Apr. 2, 1996

[54] METHOD FOR THE PREPARATION OF A SUSTAINED-RELEASE DISPENSER OF SEX PHEROMONE OF PEST INSECTS

[75] Inventors: Ryuichi Saguchi, Niigata; Kinya Ogawa, Kanagawa; Akira Yamamoto, Niigata, all of Japan

[73] Assignee: Shin-Etsu Chemical Co., Ltd., Tokyo, Japan

[21] Appl. No.: 191,611

[22] Filed: Feb. 4, 1994

Related U.S. Application Data

[63] Continuation-in-part of Ser. No. 961,129, Oct. 14, 1992, abandoned.

[30] Foreign Application Priority Data

Oct. 16, 1991 [JP] Japan .................................. 3-296482

[51] Int. Cl.$^6$ .................................................. A01N 25/28
[52] U.S. Cl. ......................... 424/408; 424/410; 424/405; 424/84
[58] Field of Search .................................. 424/405, 408, 424/410, 84

[56] References Cited

U.S. PATENT DOCUMENTS 4,923,119   5/1990   Yamamoto et al. ..................... 239/55

Primary Examiner—Thurman K. Page
Assistant Examiner—N. Levy
Attorney, Agent, or Firm—McAulay Fisher Nissen Goldberg & Kiel

[57] ABSTRACT

An improved method is proposed for the preparation of a sex pheromone dispenser used in the elimination of pest insects from the field by the disruption of mating of the insects by distributing sustained-release dispensers containing the sex pheromone compound of the insect over the field. According to the invention, pheromone dispensers made from a polyolefin-based resin and filled with the liquid pheromone are subjected, prior to distribution over the field at a relatively low temperature in early spring, to a pretreatment of keeping them at 35° to 60° C. until the dispenser walls of the polyolefin resin absorb 2 to 10% by weight of the pheromone. When the dispensers after the pre-treatment are distributed, a relatively high rate of pheromone release can be obtained at the low temperature as compared with untreated dispensers so that the rate of pheromone release can be relatively uniform over the whole period of the season in which the pheromone dispensers are kept over the field.

4 Claims, No Drawings

METHOD FOR THE PREPARATION OF A SUSTAINED-RELEASE DISPENSER OF SEX PHEROMONE OF PEST INSECTS

This is a continuation-in-part application from a U.S. patent application Ser. No. 07/961,129 filed Oct. 14, 1992 now abandoned.

BACKGROUND OF THE INVENTION

The present invention relates to a method for the preparation of a sex pheromone dispenser used in the elimination of pest insects by means of sustained release of the sex pheromone compound of the insects which, when contained in an extremely low concentration in the atmospheric air, can disturb the intercommunication between different sexes of the insects so as to disrupt mating of them. More particularly, the invention relates to a method for the preparation of a sex pheromone dispenser capable of sustainedly releasing the pheromone compound at a uniform rate even at a relatively low temperature.

As one of the methods for the elimination of pest insects from the agricultural fields, the method by the utilization of a sex pheromone compound of the specific insect species is highlighted in recent years, in which the synthetically prepared sex pheromone compound, referred to simply as pheromone hereinafter, is released to the atmosphere of the field and contained in the air so that the males of the insect are disturbed from recognition of the females to mate which releases the same pheromone compound to attract the male. This method of mating disruption is highlighted because the method is absolutely free from the problem of environmental pollution which is unavoidable in the use of a large quantity of insecticide compounds having toxicity not only against the pests but also against human body.

Since development of pest insects is repeated several times during the seasons beginning with spring and ending in autumn in the year, the method of pest elimination by use of a pheromone is usually undertaken by distributing a large number of pheromone dispensers over the field during the period in which the adult insects of the first generation develop so as to release the pheromone compound sustainedly through the summer to autumn.

Various attempts and proposals have been heretofore made in order to improve such pheromone dispensers relative to the sustained releasability of the pheromone. Following are some of the examples of those improved pheromone dispensers as proposed.

U.S. Pat. No. 4,017,030 proposes a pheromone dispenser of a type in which the pheromone compound is contained in a capillary tube closed at one end and opening at the other end and the pheromone is sustainedly released into the atmosphere out of the open end. The pheromone dispensers of this type, however, are not suitable for practical use because the amount of the pheromone compound contained in a single dispenser tube is usually very small so that the dispenser has a limited life for sustainedly releasing the pheromone.

Pheromone dispensers of a second type include those proposed in U.S. Pat. No. 4,160,335 in which a carrier layer of a polymer admixed with the pheromone is laminated with a layer of a polymer as a releasing-controlling layer to form a laminated body and those proposed in Japanese Pat. Kokai No. 59-13701 and No. 59-59734 and U.S. Pat. No. 4,445,641 in which a porous body impregnated with a pheromone is coated with a coating layer of polyethylene and the like to control the permeating rate of the pheromone therethrough. These pheromone dispensers have a defect in common that a considerably large portion of the pheromone initially contained in the dispenser remains as unreleased even after expiration of the life of the dispenser.

As the pheromone dispensers of a third type, U.S. Pat. Nos. 2,800,457, No. 2,800,458 and No. 3,577,515 propose microcapsules in which a pheromone compound is encapsulated. These pheromone-containing microcapsules, however, are far from practicality because the cost for the preparation of microcapsules is high and a considerably large portion of the expensive pheromone compound is lost in the course of the preparation of the microcapsules in addition to the defect that the rate of pheromone release is usually too large due to the large surface area of microcapsules so that the serviceable life of the pheromone dispensers of the microcapsule type cannot be long enough.

The pheromone dispensers of a fourth type are proposed in Japanese Patent Kokai No. 62-195303 and elsewhere in which a pheromone is contained in a container in the form of a capillary tube or ampule made from a uniform simple layer of a polymer film. In particular, the polymeric film material may have a specific equilibrium swelling ratio with the pheromone compound.

The container of the fourth-type pheromone dispensers is usually made from a polyolefin film of a relatively large thickness which ensures good sustained releasability of the pheromone to impart the dispenser with a long serviceable life. On the other hand, such a pheromone container causes following problems because the pheromone must permeate through the wall of the container so that the rate of pheromone release to the atmosphere largely depends on the temperature.

When the pheromone dispenser is to be used throughout the year, namely, a sufficiently high rate of release cannot be obtained under a climatic condition of low temperatures as in early spring, when most of the first-generation pest insects develop. When the barrier performance of the polymer film is decreased by using a polymer film of a decreased thickness or by using a polyolefin of a low crystallinity in order to ensure high releasability of the pheromone, on the other hand, a problem is caused that not only the rate of pheromone release is too high when the ambient temperature is high as in summer but also the liquid pheromone infiltrates the walls of the dispenser so as to increase the unavailable portion of the pheromone contained in the dispenser. When the pheromone dispenser is prepared such that the rate of pheromone release is appropriate at high temperatures of summer, on the other hand, the rate of pheromone release would be too low at low temperatures or, in particular, at the initial stage of use so that the object of pest elimination cannot be fully achieved.

When the pheromone compound is an aldehyde, acetate, ketone, hydrocarbon or alcohol of 10 to 22 carbon atoms in a molecule having aliphatic unsaturation, as is the case of most of the pheromone compounds of the insects belonging to the order of Lepidoptera, the pheromone compound infiltrating the walls of the dispenser and retained there is subject to denaturation by the reaction of polymerization, oxidation, bond cleavage and the like. This problem can of course be solved by enhancing the barrier performance of the dispenser walls though at the sacrifice of the pheromone releasability not to ensure sufficiently high rate of pheromone release at low temperatures in early spring.

SUMMARY OF THE INVENTION

The present invention accordingly has an object to provide a novel and improved method for the preparation of a sex pheromone dispenser used for disruption of mating of pest insects by the sustained release of the sex pheromone of the pest insects, in which the pheromone is prevented from denaturation by the reactions of polymerization, oxidation, bond cleavage and the like at high temperatures of summer still ensuring a sufficiently high rate of pheromone release even at low temperatures in early spring.

Thus, the method of the present invention for the preparation of a sex pheromone dispenser used for the disruption of mating of pest insects by sustainedly releasing the sex pheromone compound of the insects over the field comprises the steps of:

(a) encapsulating a liquid sex pheromone compound of the insects in a container having walls made from a uniform layer of a polyolefin resin having a wall thickness in the range from 0.2 to 2.0 mm at a temperature lower than 35 ° C. to prepare a pheromone-filled container;

(b) keeping the pheromone-filled container at a temperature in the range from 35 ° C. to 60 ° C. for such a length of time that the walls of the container contain the liquid sex pheromone compound in an amount in the range from 2% to 10% by weight based on the weight of the empty container by the infiltration of the liquid pheromone compound through the walls of the container.

DETAILED DESCRIPTION OF THE PREFERRED EMBODIMENTS

As is described above, the method of the present invention for the preparation of a sex pheromone dispenser used for the disruption of mating of pest insects by sustainedly releasing the sex pheromone of the insects over the field comprises the steps (a) for the preparation of a pheromone-filled polyolefin container and (b) the infiltration pretreatment thereof by keeping at a specified elevated temperature for a specified length of time. Elimination of the pest insects is performed by distributing a number of such dispensers so that the liquid pheromone compound of the insects is sustainedly released over the field throughout the year beginning with the early spring when the temperature is low through the summer when the temperature is high. Characteristically, with the pheromone dispensers prepared by the inventive method, elimination of pest insects is performed by distributing the pheromone dispensers prepared in a cold season over the field not as prepared but after a pretreatment in which the pheromone-containing polyolefin containers are kept at a temperature of 35° to 60° C. until the liquid pheromone compound infiltrates the walls of the container so that the polyolefin film of the dispenser walls contains a specified amount of the liquid pheromone.

The above described unique method of the present invention has been completed on the base of the following findings obtained by the extensive investigations undertaken by the inventors with an object to achieve the above mentioned object.

1) In a pheromone dispenser made from a container of a polyolefin resin filled with a liquid pheromone, the amount of the pheromone absorbed in the dispenser walls can be freely controlled by selecting the temperature and duration for the storage of the pheromone dispenser.

2) When pheromone dispensers, of which the walls contain the pheromone as absorbed therein beforehand, are distributed over the field, the rate of pheromone release can be high at the initial stage directly after distribution as compared with freshly prepared dispensers.

3) Diffusion of the pheromone molecules through the dispenser walls can be increased-when the walls contain the pheromone absorbed in advance.

4) When preliminary absorption of the pheromone in the dispenser walls is effected at a temperature higher than the temperature which the dispensers may encounter in the field during practical use thereof, the dispenser walls absorb an excessively large amount of the pheromone so that the rate of pheromone release at the initial stage can be increased so much. This is because the behavior of pheromone release through the dispenser walls is greatly influenced, in particular, at low temperatures by the solubility of the pheromone in the walls and diffusion of pheromone molecules through the walls.

5) Assuming that dissolution of the pheromone molecules in the polymeric dispenser walls causes relaxation of the polymeric molecular chains to an extent depending on the temperature so that the interstices of the thus relaxed molecular chains are filled with the pheromone molecules to determine the swelling ratio, the velocity at which the once relaxed molecular chain structure regains the unrelaxed state by losing the pheromone molecules is extremely low as compared with the velocity at which the unrelaxed molecular chain structure becomes relaxed by absorbing the pheromone molecules.

6) Assuming that the swelling ratios are the same, fluctuation of the pheromone molecules and the polymeric molecular chains is larger at higher temperatures than at lower temperatures so that the molecular chain structure is in the more highly relaxed state at higher temperatures.

Further continued investigations conducted by the inventors on the base of the above described findings have led to a discovery that the working efficiency of a pheromone dispenser made from a film of a polyolefin resin can remarkably be improved when the dispenser filled with a liquid pheromone is subjected, prior to distribution over the field, to a pre-treatment for absorption of the liquid pheromone by the dispenser walls at a temperature substantially higher than the temperature which the dispensers may encounter in the field to such an extent that the polymeric dispenser walls contain the pheromone in an amount of 2% to 10% by weight based on the weight of the walls of the empty container resulting in completion of the present invention.

It is preferable that the amount of the liquid pheromone compound contained in each of the pheromone dispensers prepared according to the inventive method is at least 30 mg since the desired duration of effectiveness obtained by a single distribution work of pheromone dispensers is at least 90 days to exhibit a full effect of mating disruption.

The polyolefin-made container of the pheromone dispenser used in the inventive method can be in the form of a capillary tube, ampule, hollow sphere, bag and the like having a uniform wall thickness shaped by a conventional molding method such as blow molding, two-stage drawing, extrusion molding, compression molding and the like. The wall thickness thereof, which greatly influences the rate of pheromone release, is preferably in the range from 0.2 to 2 mm. When the wall thickness is too small, the permeation velocity of the liquid pheromone through the wall is too large to destroy the balance between infiltration of the pheromone from the inner surface of the wall and the vaporization loss of the pheromone from the outer surface thereof so that a liquid film is eventually formed on and wet the outer surface similarly to the phenomenon of bleeding. When the thickness is too large, on the other hand, the rate of pheromone release would be so low that the working efficiency of the dispenser would be insufficiently low especially at low temperatures.

It is important that the walls of the dispensers prepared by the inventive method are formed from a uniform film of a polyolefin resin. Porous films and laminated films are less preferable. In particular, porous resin films should not be used because the scope of the inventive method consists in the control of the pheromone release rate by the infiltration of the solid, i.e. non-porous, walls with the liquid pheromone compound affecting the molecular network structure of the resin film while the release rate through a porous resin film largely depends on the porosity of the porous walls. Laminated films are also not preferred because the pheromone release rate therethrough is under the balance of distribution of the pheromone between the laminating layers.

Various kinds of olefin-based polymeric resins can be used as the material of the dispenser walls including polyethylenes, polypropylenes and polypentenes as well as copolymeric resins of these monomers and another ethylenically unsaturated monomer. Examples of particularly preferable polyolefin resins include polyethylenes and copolymeric resins of ethylene and vinyl acetate in consideration of the molecular weight and molecular polarity of the pheromone compounds.

Following is a description of the pre-treatment for the preliminary absorption or infiltration of the pheromone in the dispenser walls. Although polyolefin resins as a material of the dispenser walls are generally insoluble in liquid pheromone compounds, the resins can absorb and retain the pheromone compound in an amount of a few % to several tens of % by weight. The understanding heretofore is that the polyolefin resin as the material of the pheromone dispenser walls should be swollen with the liquid pheromone with an equilibrium swelling ratio of 2 to 6% by weight at 20° C. but it is natural that the optimum swelling ratio depends on various factors such as the kind of the polyolefin resin, kind of the pheromone compound, temperature at which the dispensers are used and so on. For example, a decrease in the crystallinity of the polyolefin resin is a factor to increase the equilibrium swelling ratio. Even with the same swelling ratio, the degree of the molecular chain relaxation in the polyolefin film forming the dispenser walls depends on the temperature and it is presumable that the molecular chain structure is in a more strongly relaxed state at a higher temperature due to the increased Brownian movement of the pheromone molecules and the polymeric molecular chains. This fact leads to a conclusion that a polyolefin film having been subjected to the pretreatment for the preliminary absorption of the pheromone at a higher temperature would return to the equilibrium state of the molecular chain structure corresponding to the ambient temperature for use of the dispenser at a lower rate than that after the pretreatment at a lower temperature even when the swelling ratios are the same to sustainedly exhibit a higher rate of pheromone release at the initial stage of use of the dispenser. Accordingly, a pheromone dispenser which should be used throughout the year beginning with early spring is subjected to the pretreatment preferably at a temperature higher than the temperature encountered in the field during use of the dispensers.

The amount of pheromone absorption in the dispenser walls of a polyolefin resin can be freely controlled in the pre-treatment by keeping a pheromone-filled dispenser at a constant temperature for an appropriate length of time selected in consideration of the nature of the polyolefin resin and the pheromone compound.

The temperature at which the pre-treatment of pheromone absorption is conducted is preferably in the range from 35° to 60° C. When the temperature is too low, not only an unduly long time is taken for the absorption of the liquid pheromone by the dispenser walls but also the relaxation of the polymeric molecular chain to be caused by the absorption of the pheromone would be insufficient so that the rate of pheromone release at the initial stage cannot be high enough. When the temperature is too high, on the other hand, the rate of pheromone release at the initial stage is unduly high and the balance between the diffusion of the pheromone molecules through the walls and evaporation thereof from the wall surface is along with a disadvantage of an unduly low rate of pheromone release as a consequence of the overly release at the initial stage.

The preferable amount of the absorbed liquid pheromone in the dispenser walls naturally depends on the amount of the pheromone initially contained in the dispenser but it is usually in the range from 2% to 10% by weight based on the empty or dry weight of the container. When the amount of absorption is too small, the rate of pheromone release at the initial stage is unduly low. When the amount is too large, on the other hand, the rate of pheromone is excessively large at the initial stage resulting in futile loss of the expensive pheromone compound.

As a particular example, it is preferable that, in a sustained-release pheromone dispenser for a pheromone which is an alcoholic compound contained in a container of a copolymeric resin of ethylene and vinyl acetate, the weight fraction of the vinyl acetate moiety in the copolymeric resin is in the range from 1 to 5%. When this weight fraction is too large, the copolymeric resin has excessively high affinity with the pheromone compound so that the resin film has an unduly high swelling ratio with the pheromone and degradation of the dispenser walls may take place by bleeding of the pheromone at high temperatures. When the weight fraction of the vinyl acetate moiety in the copolymeric resin is too small, the rate of pheromone release from the dispenser walls is limited even by the pre-treatment of pheromone absorption in the resin film although the dispenser walls are more resistant against degradation by the absorbed pheromone compound.

Assuming that the desirable amount of a pheromone absorbed in the dispenser walls made from a copolymeric resin of ethylene and vinyl acetate, of which the content of the vinyl acetate moiety is C.% by weight, is S% by weight based on the weight of the dry dispenser walls, it is preferable that the value of (S×C) is in the range from 3 to 50. This means that, when the content of the vinyl acetate moiety in the copolymeric resin is relatively high, the rate of pheromone release can be high enough so that the amount of the pheromone absorbed in the dispenser walls by the pretreatment can be relatively small to give a sufficiently large rate of pheromone release at low temperatures while, when the content of the vinyl acetate moiety in the copolymeric resin is too low, the amount of the pheromone absorbed in the dispenser walls by the pretreatment must be large in order to ensure a sufficiently high rate of pheromone release at low temperatures although the use of such a dispenser wall prevents excessively high rate of pheromone release at high temperature and degradation of the dispenser walls by bleeding of the pheromone on the dispenser walls.

As is stated before, the factors having a large influence on the rate of pheromone release include the average wall thickness and the content of the vinyl acetate moiety in the copolymeric resin of ethylene and vinyl acetate. Giving the wall thickness T in mm and the content of the vinyl acetate moiety C. in % by weight, it is preferable that the value of (T×C) is in the range from 1 to 5. This means that, in order to have the pheromone absorbed in the dispenser walls in an appropriate amount to obtain an effective rate of pheromone release, the volume or, hence, the thickness of the dispenser walls can be small when the content of the vinyl acetate moiety is high in the copolymeric resin so as to increase the swelling ratio of the resin film while, when the content of the vinyl acetate moiety is low to give a low swelling ratio of the dispenser walls with the pheromone, the volume or thickness of the dispenser walls must be increased.

In the following, the method of the invention for the preparation of a pheromone dispenser and the advantages obtained by using such dispensers are described in more detail by way of examples and comparative examples.

EXAMPLE 1

A capillary tube of high-density polyethylene having an inner diameter of 1.17 mm, wall thickness of 0.55 mm, length of 200 mm and weight of 570 mg was filled at room temperature with 175 mg of Z-8-dodecenyl acetate, which is known as the sex pheromone of Oriental fruit moth (*Grapholito molesta*) of the order of Lepidoptera, and both of the tube ends were sealed to give a pheromone dispenser. The liquid column contained in the capillary tube had a length of 195 min. The dispenser was sealed in a bag of aluminum foil and kept at 40 ° C. for 14 days so that the length of the liquid column in the capillary tube was decreased to 155 mm although absolutely no change was noted in the total weight of the dispenser tube. This meant that 36 mg of the pheromone had been absorbed in the tube wall corresponding to 6.3% by weight of pheromone absorption based on the weight of the dry capillarly tube.

A number of pheromone dispensers prepared in the above described manner and after the pre-treatment for the preliminary absorption of the pheromone in the dispenser walls were distributed over an apple orchard in Japan in early March and the weight thereof was periodically measured until the end of September to calculate the amount of the pheromone in mg released per day per dispenser for each month. The results are shown in Table 1 below.

Comparative Example 1

For comparison, the same test as above was concurrently undertaken except that the pre-treatment of the pheromone-filled dispenser tubes was omitted and the dispensers as prepared were distributed over the same apple orchard. The results are shown also in Table 1 in mg per day per dispenser for each month. As is understood from Table 1, the rate of pheromone release in this comparative example was noticeably lower than in Example 1, in particular, in the beginning stage of the test in March to April when the temperature was low.

TABLE 1

| Month | Mar. | Apr. | May | Jun. | Jul. | Aug. | Sept. |
|---|---|---|---|---|---|---|---|
| Example 1 | 0.8 | 0.8 | 0.9 | 0.9 | 1.1 | 1.1 | 0.8 |
| Comparative Example 1 | 0.3 | 0.4 | 0.7 | 0.8 | 1.0 | 1.0 | 0.8 |
| Average temperature, °C. | 14 | 16 | 18 | 19 | 22 | 23 | 16 |

EXAMPLE 2

A capillary tube of a copolymeric resin of ethylene and vinyl acetate, of which the content of the vinyl acetate moiety was 4% by weight, having an inner diameter of 1.22 ram, wall thickness of 0.55 mm, length of 200 mm and weight of 580 mg was filled at room temperature with 175 mg of E-8,E-10-dodecadienol, which is known as the sex pheromone of coding moth (*Cydia domonella*) and both of the tube ends were sealed to give a pheromone dispenser. The length of the-liquid column enclosed in the capillary tube was 195 ram.

The pheromone-filled dispenser was sealed in a bag of aluminum foil and kept at 40 ° C for 3 days so that the length of the liquid column in the capillary tube was decreased to 150 mm although absolutely no change was noted in the total weight of the dispenser tube indicating that 40.4 mg of the pheromone compound had been absorbed in the dispenser walls and the content of the pheromone absorbed in the capillary wall was 7% by weight based on the weight of the dry capillary tube.

The pheromone dispensers prepared in the above described manner and after the pre-treatment for the pheromone absorption were distributed on October 1st in a pear orchard of Australia and the weight thereof was periodically measured until the end of February of the next year to calculate the rate of pheromone release in mg per day per dispenser for each month. The results are shown in Table 2.

The results in Table 2 show that the rate of pheromone release was sufficiently high even at the low temperature of October and the rate could be controlled adequately even at high temperatures of January to February without wetness of the outer surface of the dispensers by the bleeding of the pheromone to give a relatively uniform rate of pheromone release over the whole period of test.

Comparative Example 2

The procedure of the test was just the same as in Example 2 excepting omission of the pre-treatment of the pheromone-filled dispensers for the preliminary absorption of the pheromone. The results of the test are shown also in Table 2, from which it is understood that the rate of pheromone release was insufficiently low at low temperatures in early spring of October to November.

Comparative Example 3

The procedure of the test was just the same as in Example 2 except that the resin forming the capillary tubes of the dispensers was a copolymeric resin of ethylene and vinyl acetate of which the content of the vinyl acetate moiety was 12% by weight instead of 4% by weight and the pre-treatment of the pheromone-filled dispensers for the preliminary absorption of the pheromone was omitted. The results of the test are shown also in Table 2.

As is understood from Table 2, a sufficiently high rate of pheromone release could be obtained at low temperatures in early spring but the rate of pheromone release was excessively increased as the temperature increased in summer to cause a futile loss of the pheromone from the dispensers. In addition, the surface of the dispensers was wet and sticky due to bleeding of the pheromone to cause heavy deposition of dust particles thereon which was presumably the reason for the undue decrease in the rate of pheromone release in the succeeding period of January to February.

TABLE 2

| Month | Oct. | Nov. | Dec. | Jan. | Feb. |
|---|---|---|---|---|---|
| Example 2 | 0.7 | 0.7 | 0.8 | 1.0 | 1.0 |
| Comparative Example 2 | 0.3 | 0.4 | 0.6 | 0.8 | 0.8 |
| Comparative Example 3 | 0.8 | 1.1 | 1.8 | 0.6 | 0.1 |
| Average temperature, °C. | 14 | 17 | 20 | 23 | 24 |

EXAMPLE 3

An ampule of a copolymeric resin of ethylene and vinyl acetate, of which the content of the vinyl acetate moiety was 3% by weight, having an inner volume of 5 ml, average wall thickness of 0.8 mm and weight of 1.7 g was charged at room temperature with 300 mg of E-11-tetradecenol, which is known as the sex pheromone of variegated leaf roller to prepare a pheromone-filled dispenser. One hundred ampules prepared in the above described manner were each sealed in a bag of aluminum foil and kept at 40° C. for 7 days to have the pheromone absorbed in the ampule walls. Absolutely no change was noted in the weight of the ampules by this pre-treatment. Three of the ampules were taken and the pheromone contained therein was discharged followed by three times repeated washing of the inner walls of the ampules each time with 5 ml of ether. After evaporation of the ether, the weight of the empty are pules was measured to find that the weight increase of the ampules was 50 mg per ampule on an average of the three corresponding to 2.9% by weight of the content of the pheromone absorbed in the ampule walls.

These pheromone dispensers were distributed over a 3 hectares wide apple orchard in the United States on April 12th in a distribution density of 300 dispensers per hectare to test the efficiency for the elimination of variegated leaf rollers. The results were that the mating disruption by the pheromone traps was at least 95% during the period of three months starting in April. The proportion of damaged fruits was 0.3% in the test area with distribution of the pheromone dispensers while the proportion was 2% in the control area without distribution of the pheromone dispensers.

EXAMPLE 4

A capillary tube of high-density polyethylene having an inner diameter of 1.17 mm, wall thickness of 0.55 mm, length of 200 mm and weight of 570 mg was filled at room temperature with 175 mg of Z-11-tetradecenyl acetate and both of the tube ends were sealed to give a tubular pheromone dispenser. The liquid column contained in the capillary tube had a length of 195 mm. The dispenser was sealed in a bag of aluminum foil and kept at 40° C. for 14 days so that the length of the liquid column in the capillary tube was decreased showing that 27 mg of the pheromone had been absorbed in the tube walls of each dispenser corresponding to 4.7% by weight of the absorbed pheromone compound based on the dry tube although absolutely no change was noted in the total weight of the dispenser tubes.

The tubular pheromone dispensers prepared in the above described manner were distributed in a tea garden in Shizuoka Prefecture, Japan, in early March together with the pheromone dispenser bags prepared in comparative Examples 6 and 7 described below to measure the weight decrease in mg of each of the dispensers in each of the months. The results are shown in Table 3.

Comparative Example 4

The experimental procedure was substantially the same as in Example 4 except that the pre-treatment for pheromone absorption in the dispenser walls was performed by keeping the dispensers at 25° C. for 6 months instead of keeping at 40° C. for 14 days. The amount of pheromone absorption in the tube walls was 4.7% by weight. Table 3 also shows the results obtained in the measurement of the weight decrease of the dispenser tubes. The results indicate that, although the rate of pheromone release was approximately equivalent to Example 5 in March, the rate was not duly increased in April and May reaching the level of Example 4 only in August.

Comparative Example 5

The experimental procedure was substantially the same as in Example 4 except that the pre-treatment for pheromone absorption in the dispenser walls was performed by keeping the dispensers at 70° C. for 7 days instead of keeping at 40° C. for 14 days. The amount of pheromone absorption in the tube walls was 5.8% by weight. Table 3 also shows the results obtained in the measurement of the weight decrease of the dispenser tubes. The results indicate that the rate of pheromone release was unduly high in March while the rate was subsequently decreased in April and May regaining the level of Example 4 only in August.

Comparative Example 6

A rectangular plastic film bag was prepared by heat sealing along three sides from a 63 μm thick laminated film consisting of two low-density polyethylene films of 27 μm thickness sandwiching a poly(vinylidene chloride) film of 9 μm thickness. The bag had effective dimensions of 30 mm by 40 mm with an effective surface area of 2400 mm$^2$ and had a weight of 150 mg. The bag was filled at room temperature with 160 mg of Z-11-tetradecenyl acetate, which is known as the sex pheromone of Oriental tea fortrix (*Homona magnanima*) and the bag was heat-sealed along the open mouth to complete a pheromone dispenser bag.

The above prepared pheromone dispenser was wrapped in an aluminum foil bag and kept at 40° C. for 7 days to find absolutely no decrease in the weight of the dispenser bag. To test the pheromone absorption into the bag walls, the liquid pheromone was discharged charged out of 5 dispenser bags taken from a large number of the bag dispensers prepared in the same manner and the emptied bags were washed three times each with 5 ml of ether followed by drying and the weight increase of the empty bags was measured to find an increase of about 5 mg per bag on an average of 5 bags corresponding to 3.3% by weight pheromone absorption in the bag walls.

The pheromone dispensers after the above described absorption pre-treatment were distributed over a tea garden in Shizuoka Prefecture, Japan, in early March or, namely, prior to the appearance of the first generation of the pest insets and the weight decrease in mg of the dispensers in each of the successive months until September was measured to give the results shown in Table 3 below per bag on an average.

Comparative Example 7

The experimental procedure was substantially the same as in Comparative Example 6 excepting omission of the pretreatment for pheromone absorption into the bag walls. The results of the experiment are shown in Table 3. As is understood from this table, the rate of pheromone release is unduly low in March and April when the temperature was low as compared with Example 4 in which the rate of pheromone release was considerably high already in March and April.

TABLE 3

| Month | Mar. | Apr. | May | Jun. | Jul. | Aug. | Sept. |
|---|---|---|---|---|---|---|---|
| Example 4 | 0.48 | 0.51 | 0.59 | 0.65 | 0.73 | 0.75 | 0.63 |
| Comparative Example 4 | 0.46 | 0.42 | 0.45 | 0.55 | 0.67 | 0.72 | 0.61 |
| Comparative Example 5 | 0.81 | 0.40 | 0.50 | 0.63 | 0.67 | 0.72 | 0.64 |
| Comparative Example 6 | 0.35 | 0.30 | 0.35 | 0.47 | 0.70 | 0.75 | 0.63 |
| Comparative Example 7 | 0.18 | 0.27 | 0.35 | 0.46 | 0.68 | 0.73 | 0.62 |
| Average temperature, °C. | 9.6 | 13.9 | 15.9 | 19.5 | 24.0 | 24.6 | 21.9 |

What is claimed is

1. A method for the preparation of a sex pheromone dispenser used for the disruption of mating of pest insects by sustainedly releasing the sex pheromone compound of the insects over the field which comprises the steps of:

(a) encapsulating a liquid sex pheromone compound of the insects in a container having walls made from a uniform layer of a polyolefin resin having a wall thickness in the range from 0.2 to 2.0 mm at a temperature lower than 35° C. to prepare a pheromone-filled container;

(b) keeping the pheromone-filled container at a temperature in the range from 35° C. to 60° C. for such a length of time that the walls of the container absorb the liquid sex pheromone compound in an amount in the range from 2% to 10% by weight based on the weight of the empty container by the infiltration of the liquid pheromone compound through the walls of the container.

2. The method as claimed in claim 1 in which the polyolefin resin is a copolymeric resin of ethylene and vinyl acetate.

3. The method as claimed in claim 2 in which the content of the vinyl acetate moiety in the copolymeric resin of ethylene and vinyl acetate is in the range from 1 to 5% by weight.

4. The method as claimed in claim 2 in which the amount of the sex pheromone compound encapsulated in the container is at least 30 mg.

* * * * *